United States Patent [19]
Chan

[11] Patent Number: 5,416,936
[45] Date of Patent: May 23, 1995

[54] ROLLING-MASSAGING MATTRESS OR CUSHION

[76] Inventor: Hoi C. Chan, 218-240 Castle Peak Road, Sunny Yila, Block 3, 8/F Flat A, Ting Kav, N.T., Hong Kong

[21] Appl. No.: 113,594

[22] Filed: Aug. 27, 1993

[30] Foreign Application Priority Data

Aug. 30, 1992 [CN] China .................. 92 1 10186.4

[51] Int. Cl.⁶ .................................................. A47C 27/00
[52] U.S. Cl. .................................................. 5/448; 5/906; 5/933; 601/131; 601/134; 297/452.1
[58] Field of Search ............... 5/448, 906, 933; 601/15, 19, 131, 132, 134; 297/452.1

[56] References Cited

U.S. PATENT DOCUMENTS

| | | | |
|---|---|---|---|
| 1,539,299 | 5/1925 | Cheney | 601/131 |
| 3,829,917 | 8/1974 | De Laittre et al. | |
| 3,994,290 | 11/1976 | Springer et al. | 601/131 |
| 4,330,892 | 5/1982 | Fukushima | |
| 4,509,219 | 9/1985 | Yagi | |
| 4,796,616 | 1/1989 | Panahpour | 601/131 |
| 4,924,542 | 5/1990 | Yamaguchi | |
| 5,096,188 | 3/1992 | Shen | 601/134 |
| 5,168,588 | 12/1992 | Chan | |

FOREIGN PATENT DOCUMENTS

| | | | |
|---|---|---|---|
| 0137072 | 10/1983 | European Pat. Off. | |
| 0263065A2 | 8/1987 | European Pat. Off. | |
| 437999 | 7/1991 | European Pat. Off. | 5/906 |
| 0470767A1 | 8/1991 | European Pat. Off. | |
| 2224434 | 11/1988 | United Kingdom | |
| 2234439 | 7/1990 | United Kingdom | |
| 6103 | 7/1989 | WIPO | 5/448 |

Primary Examiner—Michael J. Milano
Attorney, Agent, or Firm—Robert M. Phipps

[57] ABSTRACT

Mattresses and cushions, which have a rolling-massaging function and magnetic-therapeutic effect are described. The rolling-massaging magnetic-therapeutic mattress or cushion comprises an upper covering, an intermediate layer, an interior layer, a compound liner and a bottom covering. Between the upper covering and the intermediate layer there is provided a magnetic-therapeutic massaging layer including balls, magnetics beads, element frames and a locating substrate. The balls and magnetic beads are contained in subcavities of the element frames, rolling omni-directionally.

11 Claims, 4 Drawing Sheets

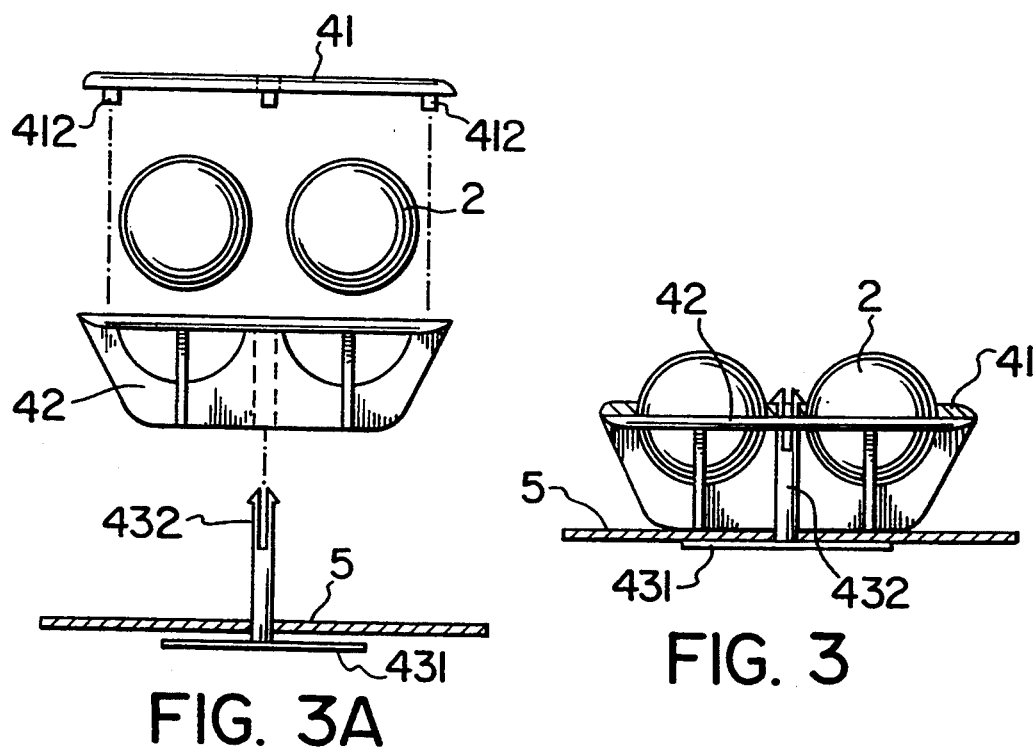
FIG. 3A
FIG. 3
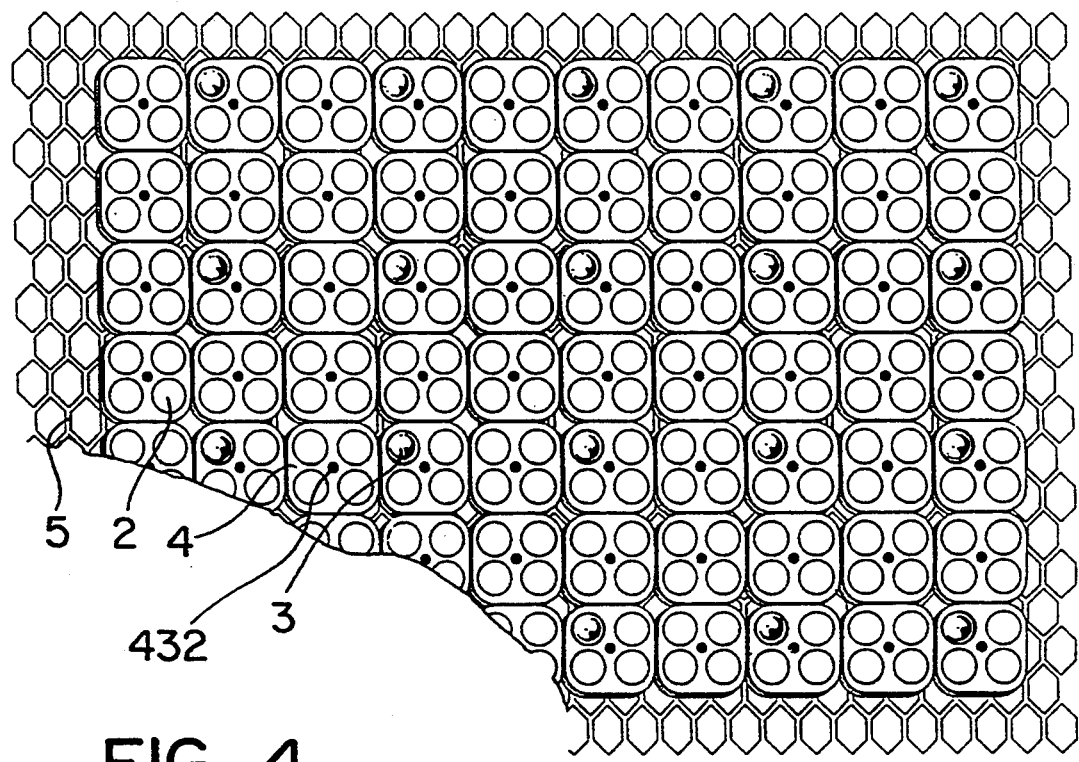
FIG. 4

ROLLING-MASSAGING MATTRESS OR CUSHION

The invention relates to personal and domestic articles, particularly to mattresses and cushion which have an rolling-massaging function and magnetic-therapeutic effect.

There are many kinds of prior art magnetic-therapeutic massaging mattresses, their construction becomes more and more exquisite and the magnetic-therapeutic function is improved continuously. They have a massaging function like being pressed by fingers, and magnetic-therapeutic effect, and have been keep-fit articles in people's daily life, e.g. the technique named "Magnetic Sleeping Mat" described in U.S. Pat. No. 5,035,017. However the known prior art mattresses have the massaging function like being pressed by fingers with the aid of many nipple projects, formed on a foamed synthetic resin board or, with the aid of an array of wooden beads and magnets adhered to a resilient interior. As the human body's movement is so slight when people sleep or sit up straight on the mattresses that the massaging function caused by it would be weaker, and the magnetic-therapeutic massaging layer of this construction contain less air so as to feel muggy when you sleep or sit on them, therefore the above-mentioned mattresses are not ideal and their uses are limited.

The object of the present invention is to compensate the drawbacks in the above-mentioned prior art techniques and to provide a kind of magnetic-therapeutic mattress or cushion that have a strong massaging effect like being pressed by fingers, and not make people feel muggy when they sleep or sit on it.

The object of the present invention can be attained by means of the following measures: to manufacture an omnidirectional-rolling-massaging magnetic-therapeutic mattress or cushion comprising an upper covering, an intermediate layer, an interior, a compound liner and a bottom covering. Between the upper covering and the intermediate layer there is provided a magnetic-therapeutic massaging layer including balls, magnetic beads, element frames and a locating substrate. The balls and magnetic beads are contained in some cavities of element frames, rolling omni-directionally. Many element frames are arranged in proper order on the locating substrate and fixed there, and form wherein a whole array of rolling bodies.

The accompanying drawings are illustrated as follows:

FIG. 3 depict element frame 4 in an assembled form;

FIG. 3A shows an exploded view of FIG. 3;

FIG. 4 is a vertical view of the magnetic-therapeutic massaging layer of the mattress, of which the upper covering (1) has been taken off;

Figure 1:
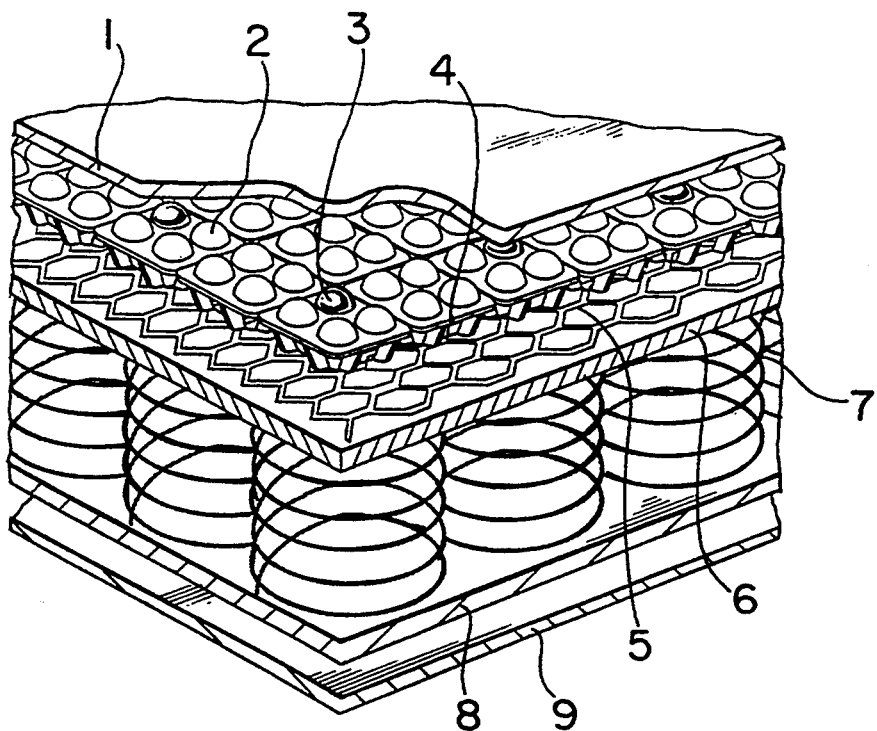
FIG. 1 is a diagrammatic construction sketch of the rolling-massaging mattress according to the present invention.

A few of preferred embodiments of the invention will further be described incorporating with the accompanying drawings as follows:

With reference to FIG. 1 of the accompanying drawings, the mattress according to the invention comprises an upper covering 1, an intermediate layer 6, a resilient interior 7, a compound liner 8 and a bottom covering 9. Between the upper covering 1 and the intermediate layer 6 there is provided a magnetic-therapeutic massaging layer including balls 2, magnetic beads 3, element frames 4 and a locating substrate 5. The balls 2 and magnetic beads 3 are contained in some cavities of element frames 4, rolling omni-directionally. Many element frames 4 are arranged in proper order on the locating substrate 5 and fixed there, and form wherein a whole array of rolling bodies as shown in FIG. 4. The resilient interior 7 of the mattress or chair according to an embodiment of the invention is generally a spiral steel spring matrix as shown in FIG. 1 so as to ventilate.

Figure 2:
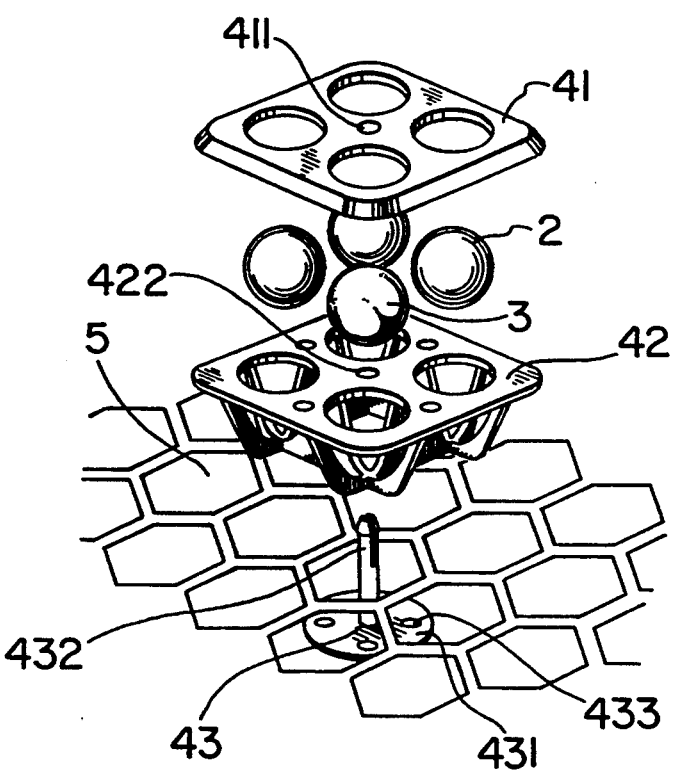
FIG. 2 is a decomposed diagrammatic sketch of the element frame (4) in the magnetic-therapeutic massaging layer of the mattress according to the invention.

As shown in FIGS. 2, 3 and 3A, the element frame 4 of mattress or cushion according to the invention comprises an upper lid 41, a frame body 42 and a fixing nail 43; the balls 2, yet the magnetic bead 8 for some, is put wherein into each cavity of the frame body 42 separately, and then the upper lid 41 is put onto the frame body 42, the seam is welded with the aid of ultrasonic. Bodies of each ball 2 and magnetic bead 3 are all projecting partially from their upper lid 41, they can't come off therefrom, as a result form thereby a rolling-massaging surface. The rod 432 of the fixing nail 43 passes through the mesh hole from the bottom of the locating substrate 5, cuts through the central fixing hole 422 of the frame body 42, and goes out from the central hole 411 of the upper lid 41, causes the element frame 4 latching onto the locating substrate 5 with the aid of the split inverted hook at the top of the nail rod 432.

The upper lid 41 of the element frame 4 is roughly a rectangular sheet, on which there are, for example, four holes in order to project the rolling surfaces of the ball 2 and magnetic bead 3 and not to get them coming off; there is at the centre of the upper lid 41 a hole 411, at the underneath surface of the upper lid 41 are disposed a few of pins 412 for locating. The upper part of the frame body 42 of the said element frame 4 is similar in form to the upper lid 41, only the hole on it are still large so as to put the balls 2 and the magnetic bead 3 into them nicely. There is at the centre of the upper part of the frame body 42 an extending hole 422 so that the rod 432 of the fixing nail 43 may cut across it. There are around the extending hole 422 several caves into which the pins 412 on the bottom surface of the upper lid 41 can be inserted for locating. The lower part of the frame body 42 is, for example, four cavities made up of some grille-like ribs for the containing of the balls 2 or the magnetic bead 3. As for the fixing nail 43 of the element frame 4, its chassis is a sheet-like foundation 431 and can be round, there are on it several ventilating holes 433.

At the centre of the foundation 431 there is disposed an erect nail rod 432, of which the top is an inverted hook which is split in the middle.

All the components made up into the element frame 4, such as the upper lid 41, the frame body 42 and the fixing nail 43 can be formed with the aid of an injection mold from a kind of high-strength engineering plastics, for example, ABS. The ball 2 contained in the cavity of the element frame 4 is a solid or porous spheroid, and can be wooden ceramic, of bamboo, solid or aerated-plastic, or sintered with stone. The magnetic bead 3 contained in the said cavity is a kind of permanently magnetic spheroid, can be made of, for example, ferrite or alnico and has a surface field-intensity of from 500 to 2,000 Gauss.

In the rolling bodies array of the magnetic-therapeutic layer in a mattress according to the invention the number proportion of the ball 2 to the magnetic bead 3 is several to one, up to tens to one. The optimum is ten and several to one, for example, there are disposed in the said array only one row or one column of the miscellaneous line consisting of the ball 2 and magnetic bead 3 every three lines of the unitary ball 2 as shown in FIG. 4.

Figure 5:
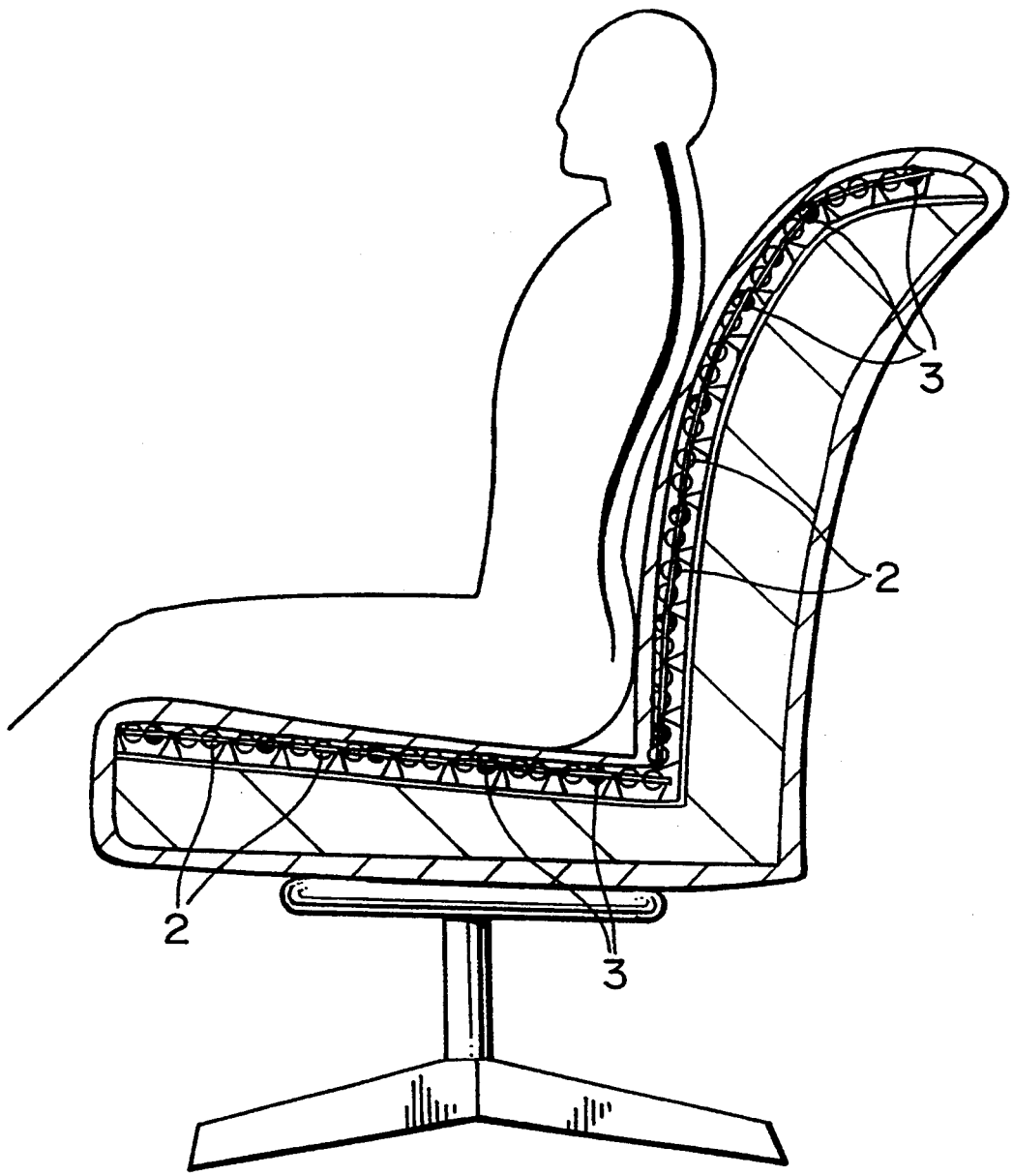
FIG. 5 is a diagrammatic sketch of the cushion and the back of a chair according to an embodiment of the invention.
Figure 6:
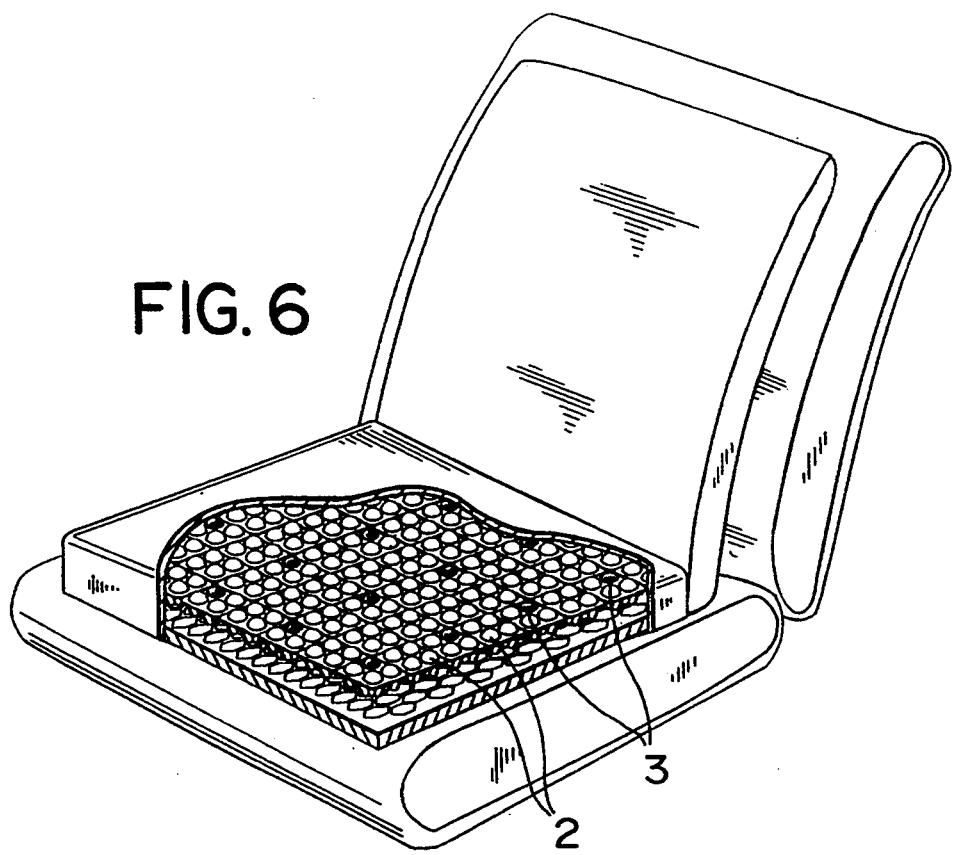
FIG. 6 is a diagrammatic construction sketch of that cushion of a chair according to the invention, which the upper covering 1 has partially been taken off.
Figure 7:
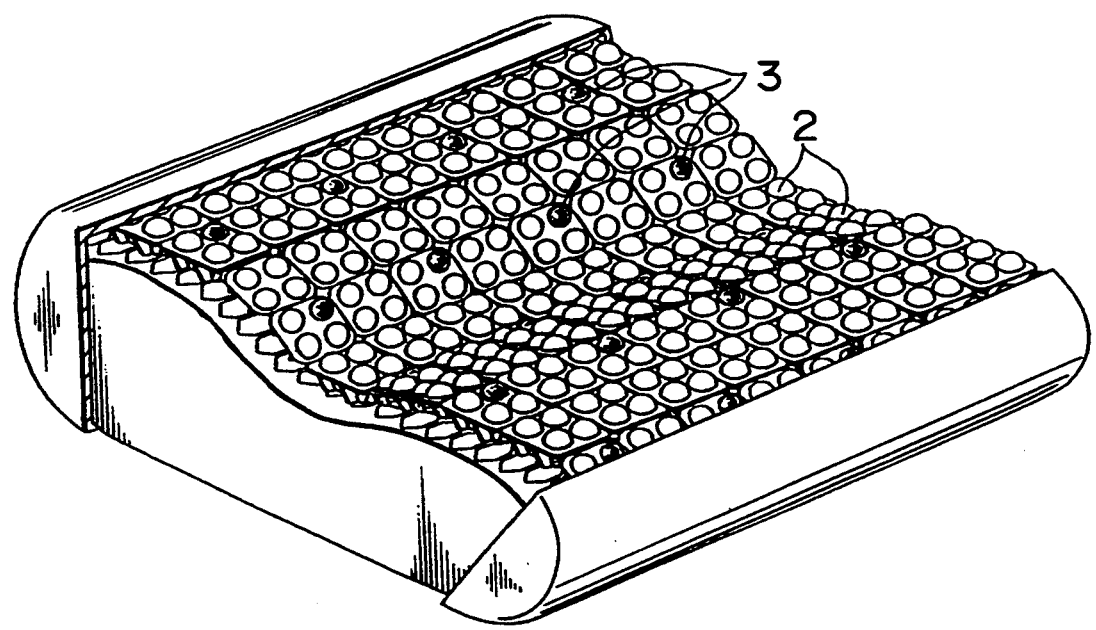
FIG. 7 is a diagrammatic construction sketch of that pillow according to the invention, off which the upper covering (1) has partially been taken off.

The cushion and the back according to an embodiment of the invention, is shown in FIG. 5 and 6, and the pillow according to an embodiment of the invention is shown in FIG. 7. The latter is a kind of appliances for being pillowed having a waved cross section, pillowing on this kind of appliances people will feel extremely comfortable. In the both embodiments the said resilient interior 7 is often made of a plastics foam material or coconut fibre etc.

Using a mattress or cushion according to the invention will not only achieve the well-know magnetic-therapeutic result, but also strongly experience the finger-pressing massaging efficacy. In the magnetic-therapeutic layer of a mattress or cushion according to the invention every rolling body can roll omni-directionally. There is a frame body 42 of element frames 4 underneath the rolling bodies 2 and 3, which are several cavities made up of some grille-like ribs and contain a lot of air. As the upper covering I on the rolling bodies 2 and 3 is so thin that when the human skin touches it the rolling massaging effect is very strong though the human body's movement is slight; besides, the massaging effect makes air circulated, thus reducing the human skin's temperature. As the rolling massage produces less electrostatic charge, the mattress or cushion is very comfortable. As the spiral steel spring matrix is used for the resilient interior 7, the ventilating effect is further enhanced and the drawback of an escaping of that chemicals is avoided which are some decomposed products from the resilient interior 7 because of using a plastics foam material. The measuring shows that the temperature of the contacting place between the human skin and the mattress or cushion is up to 40° C. when people sleep or sit on a common mattress or cushion, but the temperature of the contacting place is only 35° C. when sleep or sit up straight on the mattress or cushion according to the invention, it will be more comfortable in a room without air-conditioner, especially in summer.

Compared with the prior art, the advantages of the rolling massaging mattress or cushion according to the present invention are as follows: people can not only achieve the magnetic-therapeutic result, especially experience a strong finger-pressing massaging efficacy. The said mattress or cushion has good ventilation, produces less electrostatic charge, does not escape chemicals, and is especially suitable for office workers and people suffering from skin diseases.

I claim:

1. A rolling-massaging mattress or cushion comprising:

an upper covering, an intermediate layer, a resilient interior, a compound liner and a bottom covering, characterized in that between the upper covering and the intermediate layer there is provided a magnetic-therapeutic massaging layer including balls, magnetic beads, element frames and a locating substrate, the balls and magnetic beads are contained in cavities of said element frames, rolling omnidirectionally, a plurality of element frames are arranged in proper order on the locating substrate and fixed there, and form wherein a whole array of rolling bodies.

2. A rolling-massaging mattress or cushion according to claim 1, characterized in that the said element frame comprises an upper lid, a frame body and a fixing nail, the bails and the magnetic beads are placed into each cavity of the frame body and then the upper lid is attached onto the frame body; each of said ball and magnetic bead are partially projected from the upper lid thereby providing a rolling-massaging surface; the fixing nail comprises a rod which passes through a mesh hole at the bottom of the locating substrate, cuts through a central fixing hole of the frame body and exits out from a central hole of the upper lid thus the element frame is attached onto the locating substrate with the aid of a split inverted hook at the top of the nail rod.

3. A rolling-massaging mattress or cushion according to claim 2, characterized in that the upper lid of the said element frame is a quasi-rectangular sheet, on which there are four holes in order to project the rolling surfaces of the ball and magnetic bead; there is at the centre of the upper lid a hole, at the underneath surface of the upper lid are disposed a plurality of pins for locating said upper lid on said frame body.

4. A rolling-massaging mattress or cushion according to claim 2, characterized in that the upper part of the frame body of the said element frame is similar in form to the upper lid; the upper part of the frame body contains holes which are larger than the holes in the upper lid; there is at the centre of the upper part of the frame body an extending hole so that the rod of the fixing nail may pass through it; the frame body also comprises several caves into which the pins on the bottom surface of the upper lid can be inserted for locating; the lower part of the frame body comprises four cavities of some grill-like ribs for containing the ball or the magnetic bead.

5. A rolling-massaging mattress or cushion according to claim 2, characterized in that the fixing nail of the element frame comprises a chassis of a sheet-like foundation comprising several ventilating holes, at the centre of the foundation there is disposed the erect rod, of which the top is an inverted hook which is split in the middle.

6. A rolling-massaging mattress or cushion according to claim 2, characterized in that the components comprising the element frame, such as the upper lid, the frame body and the fixing nail can be formed with the aid of an injection mold from a type of high-strength engineering plastic.

7. A rolling-massaging mattress or cushion according to claim 1, characterized in that the said ball is a solid or porous spheroid, and can be selected from the group consisting of wood, ceramic, bamboo, solid plastic or aerated-plastic, and sintered stone.

8. A rolling-massaging mattress or cushion according to claim 1, characterized in that the said magnetic bead is a permanently magnetic spheroid, and has a surface field-intensity of from 500 to 2,000 Gauss.

9. A rolling-massaging mattress or cushion according to claim 1, characterized in that the number proportion of ball to magnetic bead, in said magnetic-therapeutic layer, is several to one, to up to ten to one.

10. A rolling-massaging mattress or cushion according to claim 1, characterized in that the said resilient interior of the mattress or cushion is generally a spiral steel spring matrix so as to ventilate.

11. A rolling-massaging mattress or cushion according to claim 8, wherein said permanently magnetic spheroid is ferrite or alnico.

* * * * *

UNITED STATES PATENT AND TRADEMARK OFFICE
CERTIFICATE OF CORRECTION

PATENT NO. : 5,416,936
DATED      : May 23, 1995
INVENTOR(S) : Hoi Chau Chan

It is certified that error appears in the above-identified patent and that said Letters Patent is hereby corrected as shown below:

Title page, Item (76) Inventor:
    The name Hoi "C." Chan should read Hoi -- Chau -- Chan;
    In the address Sunny "Yila" should read Sunny -- Yilla --;
    and Ting "Kav" should read Ting -- Kau --.

Signed and Sealed this

Tenth Day of October, 1995

Attest:

BRUCE LEHMAN

Attesting Officer     Commissioner of Patents and Trademarks